(12) United States Patent
Chen et al.

(10) Patent No.: US 6,306,435 B1
(45) Date of Patent: Oct. 23, 2001

(54) ORAL PHARMACEUTICAL PREPARATION EMBEDDED IN AN OILY MATRIX AND METHODS OF MAKING THE SAME

(75) Inventors: Gan-Lin Chen; Wen-Yi Hsu, both of Taichung (TW)

(73) Assignee: Yung Shin Pharmaceutical Industrial Co. Ltd., Ta-Chia, Taichung (TW)

( * ) Notice: Subject to any disclaimer, the term of this patent is extended or adjusted under 35 U.S.C. 154(b) by 0 days.

(21) Appl. No.: 09/603,907

(22) Filed: Jun. 26, 2000

(51) Int. Cl.$^7$ ...................................................... A61K 9/52
(52) U.S. Cl. ........................ 424/457; 424/451; 424/455; 424/456; 424/463
(58) Field of Search .................................. 424/463, 451, 424/452, 455, 457, 462, 456

(56) References Cited

U.S. PATENT DOCUMENTS

| | | |
|---|---|---|
| 4,255,431 | 3/1981 | Junggren et al. . |
| 4,786,505 * | 11/1988 | Lovgren et al. ...................... 424/468 |
| 4,853,230 | 8/1989 | Lovgren et al. . |
| 5,232,706 | 8/1993 | Coll . |
| 5,464,631 * | 11/1995 | Hoover et al. ........................ 424/454 |
| 5,714,504 * | 2/1998 | Lindberg et al. ..................... 514/338 |
| 5,733,880 | 3/1998 | Mincher . |
| 5,814,338 | 9/1998 | Veronesi . |
| 5,916,590 | 6/1999 | Cody et al. . |
| 6,063,927 | 5/2000 | Craig et al. . |

FOREIGN PATENT DOCUMENTS 0 124 495  2/1984  (EP) .

* cited by examiner

Primary Examiner—Thurman K. Page
Assistant Examiner—Rachel M. Bennett
(74) Attorney, Agent, or Firm—Fei-Fei Chao; Venable, Baetjer, Howard & Civiletti, LLP

(57) ABSTRACT

The present invention relates to an oral pharmaceutical preparation which contains an acid or base labile pharmaceutical ingredient which is embedded in an oily matrix which is controlled at neutral pH. The oily matrix-embedded pharmaceutical ingredient is encapsulated and then being coated by an enteric coating. The enteric coating enables the pharmaceutical ingredient to reach the small intestine for absorption. The oily matrix has the advantages of avoiding acidic or basic conditions. It can also isolate moisture and oxygen so as to allow for greater absorption and bioavailability of the pharmaceutical ingredient in vivo.

18 Claims, 4 Drawing Sheets

ORAL PHARMACEUTICAL PREPARATION EMBEDDED IN AN OILY MATRIX AND METHODS OF MAKING THE SAME

FIELD OF THE INVENTION

The present invention relates to a novel oral pharmaceutical preparation wherein the active pharmaceutical ingredient is acid or base labile. The pharmaceutical preparation is characterized by having the acid or base labile pharmaceutical ingredient embedded in an oily matrix, preferably at about neutral pH. The oily matrix primarily includes oils, fats, waxes, and/or sterols. The preferred oily matrix includes mineral oil, hydrogenated vegetable oil, paraffin, squalane, vaseline, and/or lanolin, which can be used singly or in any combination. The oily matrix-embedded acid or base labile pharmaceutical ingredient is placed in a capsule, which is coated by an enteric coating.

The present invention also relates to methods for producing the pharmaceutical preparation.

BACKGROUND OF THE INVENTION

For an active pharmaceutical ingredient which is slightly soluble in water and which rapidly degrades in an acid or base environment, there is a limited number of options as far as pharmaceutical development is concerned. The conventional way to prevent early degradation of the acid or base labile pharmaceutical ingredient is to preserve the ingredient in a micro-pH environment by combining the ingredient with alkaline salts/alkaline compound (i.e., for acid labile pharmaceutical active ingredient) or acid salt/acid compounds (i.e., for base labile pharmaceutical active ingredient).

For example, some of the substituted benzimidazole compounds, as described in U.S. Pat. Nos. 4,255,431 and 4,853,230, have possessed acid labile properties. Such substituted benzimidazoles are a group of compounds which are well known for their pharmacological effects for treating patients with gastrointestinal disorders. These compounds, due to their acid labile characteristics, present a problem for oral formulations, because oral intake of the compounds involves direct contact with acidic gastric juices, which may result in early decomposition of the compounds.

One of these substituted benzimidazole compounds, omeprazole, is especially known for its activity as an inhibitor of $H^+K^+$-ATPase and the proton pump in the gastric mucosa. Omeprazole has the formula of 5-methoxy-2(((4-methoxy-3,5-dimethyl-2-pyridinyl)methyl)sulfinyl)-1H-benzimidazole). Omeprazole can be used for the treatment of gastritis, gastric, peptic, and duodenal ulcers (U.S. Pat. Nos. 4,255,431, 4,786,505, and EPO 124495) as well as Zollinger-Ellison syndrome. In a more general sense, omeprazole may be used for prevention and treatment of other gastrointestinal disorders where cytoprotective and/or gastric antisecretory effect is desirable, e.g., in patients with gastrinomas, in patients with acute upper gastrointestinal bleeding, and in patients with a history of chronic and excessive alcohol consumption.

Omeprazole is very slightly soluble in water, but is very soluble in alkaline solutions in the form of a negatively charged ion. It is an ampholyte with pKa~4 (pyridinium) and 8.8 (benzimidazole). Omeprazole degrades very rapidly in water solutions at low pH values. The rate of degradation proceeds with a half-life of less than 10 minutes at pH-values below 4. At pH 6.5 the half-life of degradation is 18 hours; at pH 11 about 300 days. In addition, moisture, organic solvents and acidic substances have a deleterious effect on the stability of omeprazole. (Pilbrant and Cederberg, *Scand. J. Gastroenterology* (1985) 20:113–120). Because a fully bioavailable dosage form of omeprazole must release the active drug rapidly in the proximal part of the gastrointestinal canal, a conventional oral dosage form since, inter alia, more than half of omeprazole will be degraded before reaching the small intestine.

Various pharmaceutical formulations of omeprazole have been described. For example, U.S. Pat. No. 4,255,431 describes pharmaceutical preparations of omeprazole in tablets and granules dosage forms. The preparations adopt conventional principles by mixing omeprazole with a binding agent to form moistened granules, which then can be compressed into tablets. The pharmaceutical preparations do not contain an enteric coating, which is a conventional way to prevent an acid labile substance from contact with the acidic gastric juice.

Pilbrant and Cederberg, *Scand. J. Gastroenterology* (1985) 20:113–120, describes an enteric coated dosage form of omeprazole, which, according to their clinical studies, has shown acceptable storage ability. However, such an enteric coated dosage form is unsuitable for long-term storage because the enteric coating is made of acidic compounds. When omeprazole is covered with such an acidic enteric coating, it rapidly decomposes; and the dosage form is badly discolored and decreased in omeprazole content.

U.S. Pat. No. 4,786,505 describes an oral pharmaceutical preparation of omeprazole which contains three distinctive layers: (a) a core which contains omeprazole plus an alkaline reacting compound, an alkaline omeprazole salt plus an alkaline reacting compound, and an alkaline omeprazole salt alone; (b) an inert subcoating which contains tablet excipients and polymeric film-forming compounds; and (c) an enteric coating. This invention differs from U.S. Pat. No. 4,255,431 and Pilbrant and Cederberg's disclosures for its "micro-alkaline pH" core and the inert subcoating which separates the omeprazole core from the enteric coating.

U.S. Pat. No. 5,232,706 describes an oral dosage form of omeprazole which contains (a) a nucleus containing omeprazole or an alkali salt of omeprazole mixed with a basic compound; (b) an intermediate coating formed by an excipient and a basic compound; and (c) an enteric coating. The mixture of compounds of the nucleus can be formulated as pellets, tablets, or gelatin capsule. This invention differs from U.S. Pat. No. 4,786,505 for it contains basic compounds in both the nucleus and the intermediate coating.

The present invention introduces novel pharmaceutical preparations which are suitable for acid or base labile pharmaceutical ingredients. The pharmaceutical preparations are characterized by embedding the acid or base labile pharmaceutical ingredient in an oily matrix, which is preferred to be controlled at neutral pH. The oily matrix-embedded pharmaceutical ingredient is placed into a capsule which is then enteric coated.

In particular, the present invention differs from the prior art omeprazole formulations in the following respects: First, the present invention uses an oily matrix which are controlled at neutral pH as stabilizers to preserve omeprazole. Second, the oily matrix-embedded omeprazole can be in a free base form (i.e., free of alkaline salts or alkaline compounds, or mixed with alkaline or basic compounds) and still afford the same, or better, bioavailability and storage stability as the alkaline form of omeprazole. Third, the present invention uses a capsule as a separation layer to insulate omeprazole from the enteric coating. Fourth, the present invention contains an enteric coating deposited on the capsule. Finally, due to the special effects of the oily matrix, the present pharmaceutical preparation has the advantages over the prior art formulations for its superior resistance to acid media, higher bioavailability, and greater absorption in vivo.

SUMMARY OF THE INVENTION

The present invention provides an oral pharmaceutical preparation and methods of producing this oral pharmaceutical preparation. The oral pharmaceutical preparation contains a pharmaceutically active ingredient which is acid or base labile. This active ingredient is embedded in an oily matrix. The oily matrix-embedded active pharmaceutical ingredient is enclosed in a capsule. The capsule is coated with an enteric coating.

Examples of the active ingredients include, but are not limited to, proton pump inhibitor (e.g., omeprazole [5-methoxy-2(((4-methoxy-3,5-dimethyl-2-pyridinyl) methyl)-sulfinyl)-1H-benzimidazole)], lansoprazole [2-(((3-methyl-4-(2,2,2-trifluoroethoxy)-2-pyridyl)methyl)-sulfinyl)benzimidazole]; esters (e.g., aspirin, alkaloids, dexamethasone sodium phosphate, estrone sulfate, nitroglycerin); lactones (e.g., pilocarpine, spironolactone); amides (e.g., thiacinamide, chloramphenicol); lactams (e.g., penicillins, cephalosporins); oximes (e.g., steroid oximes); imides (e.g., glutethimide, ethosuximide); malonal ureas (e.g., barbiturates); phenols (e.g., phenols in steroids); catecholamines (e.g., epinephrine, dopamine, isoproterenol); ethers (e.g., diethylether); thiols (e.g., dimercaprol); thioethers (e.g., phenothiazines; chlorpromazine); carboxylic acids (e.g., fatty acids); nitrite (e.g., amyl nitrite); and aldehydes (e.g., paraldehyde). The preferred active ingredient is the proton pump inhibitor, particularly omeprazole. If the active ingredient is omeprazole, it is preferred that omeprazole is in a free base form (i.e., the form as given in the chemical formula without salt forming components present).

The term "oily matrix" is herein defined as "any oily or greasy substances which can be used singly or in any combination and which are capable of accepting active pharmaceutical ingredient(s)". Examples of the oily matrix include, but are not limited to, oils (e.g., vegetable oil, animal oil, or mineral oil, preferably mineral oil), fats, waxes, sterols, steroids, fatty acid esters, phospholipids, hydrocarbons, higher alcohols, higher alcohol ether of a polyhydric alcohol, and a homo- or copolymer of an alkylene oxide, which can be used singly or in any combination. The preferred substances of the oily matrix includes mineral oil, hydrogenated vegetable oil, paraffin, squalane, vaseline, and lanolin. Paraffin is defined to include a mixture of hydrocarbons having the formula of $C_nH_{2n+2}$. It is preferred that the oily matrix is controlled at about neutral pH.

The weight ratio between the active ingredient and the lipid ranges between 1:1 to 1:10, preferably 1:1 to 1:5.

The oily matrix-embedded pharmaceutical ingredient further contains an excipient. Examples of the excipient includes, but not limited to, lactose, sucrose, sorbital, mannitol, starch, amylopectin, cellulose, microcrystalline cellulose, talc, gelatin, and polyvinyl alcohol.

The capsule can be a hard capsule or a soft capsule. Examples of the capsular materials include, but not limited to, natural gelatin, pectin, casein, collagen, protein, modified starch, polyvinyl pyrrolidone.

The enteric coating is made of carbohydrate polymers or polyvinyl polymers. Examples of the enteric coating materials include, but not limited to, cellulose acetate phthalate, cellulose acetate succinate, cellulose hydrogen phthalate, cellulose acetate trimellitate, ethyl cellulose, hydroxypropyl-methylcellulose phthalate, hydroxypropylmethylcellulose acetate succinate, carboxymethyl ethylcellulose, starch acetate phthalate, amylose acetate phthalate, polyvinyl acetate phthalate, polyvinyl butyrate phthalate, styrene-maleic acid copolymer, methyl-acrylate-methacrylic acid copolymer (MPM-05), methylacrylate-methacrylic acid-methylmethacrylate copolymer (MPM-06), and methylmethacrylate-methacrylic acid co-polymer (Eudragit L & S). Optionally, the enteric coating contains a plasticizer. Examples of the plasticizer include, but not limited to, triethyl citrate, triacetin, and diethyl phthalate.

The invention provides two methods for the production of the oral pharmaceutical preparation. The first method comprises the steps of: (1) mixing an active pharmaceutical ingredient with an oily matrix to form an oily matrix embedded-pharmaceutical complex; (2) filling the oily matrix embedded-pharmaceutical complex in a capsule; and (3) coating the capsule with an enteric coating. The water content of the final dosage form is preferred not to exceed 1.4% by weight.

In the second method, the oily matrix is first filled into the capsule. Then, the active pharmaceutical ingredient is added to the oily matrix-filled capsule. Finally, the capsule is covered with an enteric coating. The water content of the final dosage form is preferred not to exceed 1.4% by weight The enteric coating is coated onto the capsule by methods such as by immersion, pan coating, centrifugation, or by using a fluidized bed apparatus (e.g., a Glatt machine).

The present invention also includes a method for treating patients with gastrointestinal diseases. The method requires giving the patients a therapeutically effective amount of the oral dosage of pharmaceutical preparation containing a proton pump inhibitor such as omeprazole.

DETAILED DESCRIPTION OF THE INVENTION

Figure 1:
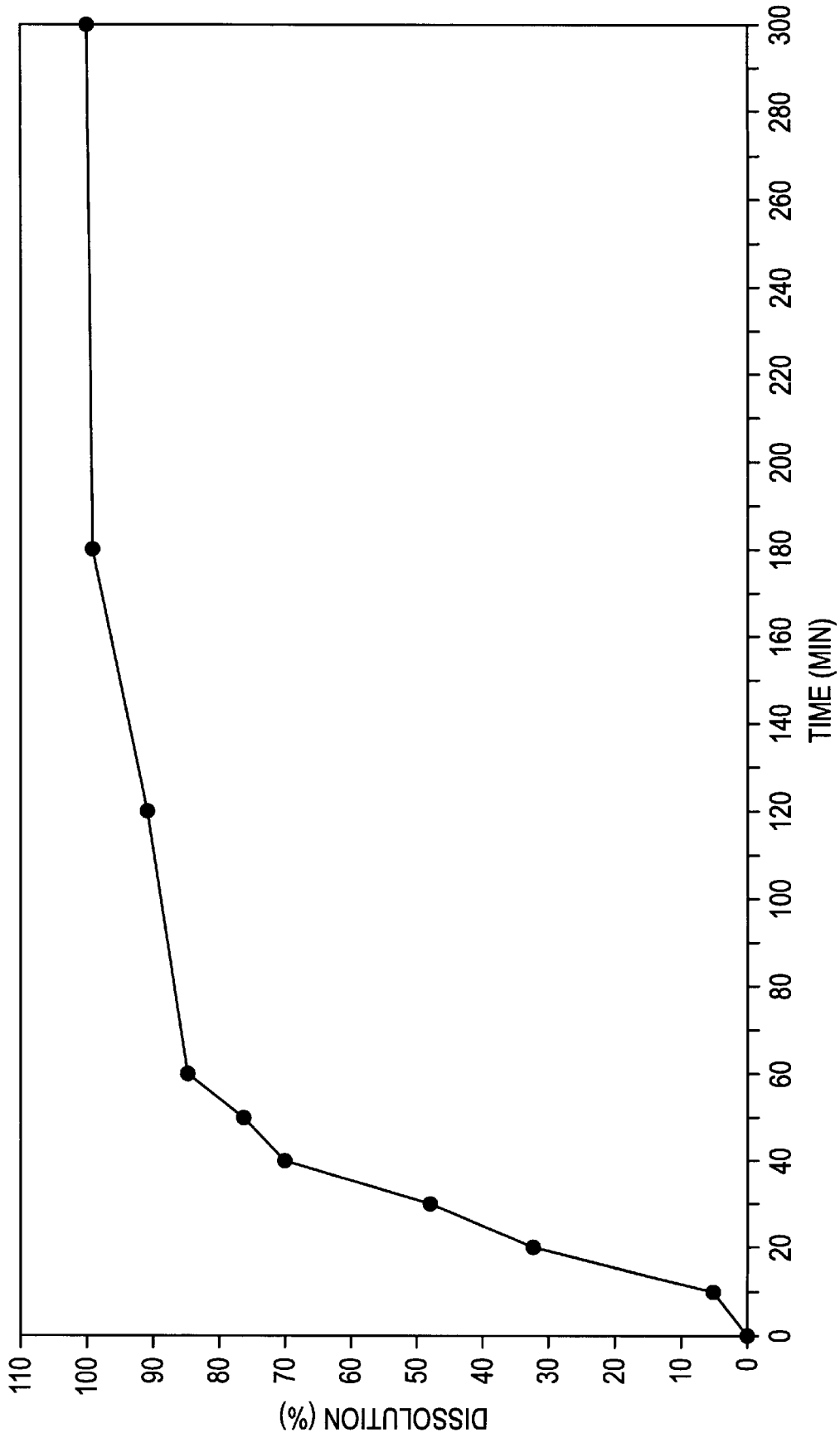
FIG. 1 shows the results of an in vitro dissolution test (% dissolution) for the enteric coated pharmaceutical preparation according to Example 1 (infra). The test was conducted according to the USP XXIII enteric coated dissolution method B. Typically, the enteric coated capsule was placed inside a hollow spiral steel device (so as to prevent the capsule from floating out of the water) which was set in a water bath. The temperature of the water bath was set at 37±0.5° C. The water bath was rotated at 50 rpm. The test contained two stages. At the first stage, the enteric coated capsule was put in the water bath containing 1000 ml of 0.1 N HCl and rotated at 50 rpm for 2 hours. Then, the HCl solution was aspirated out and replaced with 1000 ml of phosphate buffer (pH 6.8) to continue the second stage of the dissolution test. The results were determined by UV quantitation.

The present invention provides oral pharmaceutical preparation which contains an active pharmaceutical ingredient which is acid or base labile. The preferred active pharmaceutical ingredients include, but not limited to, omeprazole, lansoprazole, pentoprazole, aspirin, alkaloid, dexamethasone sodium phosphate, estrone sulfate, nitroglycerin, pilocarpine, spironolactone, thiacinamide, chloramphenicol, penicillin, cephalosporin, steroid oximes, gluethimide, ethosuximide, barbiturates, phenols in steroids, epinephrine, dopamine, isoproterenol, diethylether, dimercaprol, phenothiazines, chlorpromazine, fatty acids, amyl nitrite, and paraldehyde.

The acid or base labile pharmaceutical ingredient is embedded in an oily matrix. The oily matrix can stabilize any acid and/or base labile pharmaceutical ingredients because it can insulate the active ingredients from being contacted with moisture and oxygen. The oily matrix-embedded pharmaceutical ingredient is then placed into a capsule, which is then covered by an enteric coating.

The term "oily matrix" used in the present invention is defined as "any oily or greasy substances which can be used singly or in any combination and which are capable of accepting active pharmaceutical ingredient(s)". It includes any natural or synthetic compounds consisting of acyl carriers, such as glycerol, sphingosine, sterol, and others or derivatives thereof, to which one or more fatty acids are or can be linked. The types of substances which are suitable for use in the oily matrix include, but not limited to, oils, fats, waxes, and sterols.

Oils and fats are primarily made of triglycerides which are characterized by a glycerol linking to three fatty acids. Fats are essentially the hardened oils which are normally made by glycerol esters containing higher fatty acids, e.g., tristearine. An example of the fats which is suitable for the present pharmaceutical preparation is lanolin.

There are three major kinds of oils, which are vegetable oils, animal oils, and mineral oils. The preferred oil is mineral oil and hydrogenated vegetable oil, although other vegetable oils such as castor oil, rapeseed oil, cinnamon oil, clove oil, coconut oil, corn oil, cotton seed oil, eucalyptus oil, olive oil, palm oil, peanut oil, peppermint oil, persic oil, sassafras oil, sesame oil, soybean oil can also be used.

Examples of the waxes include paraffin, carnauba wax, candelilla wax, sugarcane wax, beeswax, cetyl esters wax, montan wax, spermaceti wax, shellac wax, microcrystalline wax, and vaseline. The preferred wax is paraffin and/or vaseline.

Some complex lipids, such as phospholipids and glycolipids, are also suitable for use in the pharmaceutical preparation. Phospholipids and glycolipids are lipids with both amphiphatic and amphiphilic characteristics. Examples of phospholipids include phosphatidylcholine, sphingomyelin, phosphatidylinositol, and phosphadityl-ethanolamine. Examples of glycolipids include cerebrosides, gangliosides, sulfolipids, and ceramides.

In addition to the above mentioned substances, a molecule that contains a substantial hydrocarbon portion may also be used in the oily matrix. For example, a hydrocarbon itself, a higher alcohol, a fatty acid ester, a higher alcohol ether of a polyhydric alcohol, a homopolymer or copolymer of an alkylene oxide and the like.

Examples of hydrocarbons include an aliphatic hydrocarbon of about 17–60 carbon atoms, such as n-heptadecane, n-octadecane, n-nonadecane, n-icosane, n-henicosane, n-docosane, n-tricosane, n-tetracosane, n-pentacosane, n-triacontane, n-tetracontane, n-pentacontane and n-hexacontane, and a mixture of these hydrocarbons.

The higher alcohols include saturated alcohols and unsaturated alcohols. Examples of the higher alcohol include lauryl alcohol, tetradecyl alcohol, myristyl alcohol, cetyl alcohol, stearyl alcohol, arachyl alcohol, higher alcohols collectable from naturally-occurring fats and oils and a mixture of these alcohols. The higher alcohol may contain about 10 to 35 of carbon atoms. Among them, a saturated higher alcohol of about 16 to 22 carbon atoms may be practically employed.

The fatty acid ester may be an ester of monohydric higher alcohol with a fatty acid (wax ester) such as cetyl palmitate, ceryl palmitate, myricyl palmitate, ceryl cerotate and melissyl melissate. It can also be an ester of a polyhydric alcohol (i.e., having two or more hydroxyl groups in the molecule with a fatty acid). Examples of the polyhydric alcohol include alkylene glycols such as ethylene glycol and propylene glycol; poly(allylene glycol) such as diethylene glycol, triethylene glycol, poly(ethylene glycol), dipropylene glycol, tripropylene glycol, poly(propylene glycol) and copolymers of these glycols; polyhydric alcohols such as glycerin, polyglycerin and pentaerythritol. Examples of saturated fatty acids include acetic acid, propionic acid, butyric acid, pelargonic acid, lauric acid, myristic acid, palmitic acid, heptadecylic acid, stearic acid, behenic acid, nonadecanoic acid and undecylic acid. Examples of the unsaturated fatty acid includes oleic acid, sorbic acid, linoleic acid, linolenic acid, arachidonic acid and stearolic acid.

The higher alcohol ether of polyhydric alcohol includes, for example, ethers formed by etherification of a polyhydric alcohol with a higher alcohol (e.g., the higher alcohols mentioned above, as well as oleyl alcohol, octyl alcohol, decyl alcohol and the like). Typical examples of the higher alcohol ethers include polyoxyethylene higher alcohol ethers (e.g., polyethylene lauryl alcohol ether, polyoxyethylene cetyl alcohol ether, polyoxyethylene stearyl alcohol ether, polyoxyethylene oleyl alcohol ether, polyoxyethylene octyl alcohol ether, polyoxyethylene decyl alcohol ether, etc.); polyoxypropylene polyoxyethylene higher alcohol ethers (e.g., polyoxypropylene polyoxyethylene cetyl alcohol ether, polyoxypropylene polyoxyethylene stearyl alcohol ether, polyoxypropylene polyoxyethylene oleyl alcohol ether, polyoxypropylene polyoxyethylene octyl alcohol ether, polyoxypropylene polyoxyethylene lauryl alcohol ether, etc.).

The polymer of alkylene oxide may be a homopolymer of alkylene oxides such as ethylene oxide, propylene oxide, trimethylene oxide and tetrahydrofuran, or a copolymer of alkylene oxide. The preferred alkylene oxide is ethylene oxide.

Examples of the homopolymer of alkylene oxide include those having a molecular weight of about 1,000 to 50,000, preferably about 1,500 to 30,000 (e.g., polyethylene glycol 6,000) and the like.

The copolymer of an alkylene oxide includes a copolymer of two or more species of the above mentioned alkylene oxides, which has a molecular weight of about 1,000 to 50,000. A copolymer containing an oxyethylene unit obtainable by copolymerizing ethylene oxide and other alkylene oxide, practically a copolymer formed with ethylene oxide and propylene oxide can be employed.

Preferred examples of the alkylene oxide polymer include a homo- or copolymer of ethylene oxide, especially polyethylene glycol.

The most favorable oily matrix includes mineral oil, hydrogenated vegetable oil, paraffin, squalane, lanolin, and vaseline, which can be used singly or in any combination.

The oily matrix-embedded pharmaceutical ingredient is encapsulated in a capsule. The conventional capsules, which are primarily made of gelatin, can be used for this purpose. The gelatin capsules are generally comprised of natural or synthetic polymers. The capsule components include natural gelatin, pectin, casein, collagen, protein, modified starch, polyvinyl pyrrolidone and the like. Gelatin is the composition of choice. These capsules may be presented as either hard or soft gelatin capsule, with the latter one containing suitable plasticizers (e.g., glycerol or sugars). In the case of soft gelatin capsules, conventional additives such as coloring agents, opacifiers and preserving agents are also added. The capsules used for the present pharmaceutical preparation may or may not contain basic compounds, such as basic amino acids (e.g., arginine, lysine, histidine, or tryptophan. It is preferred that the capsules do not contain basic compounds.

One of the advantages of embedding the pharmaceutical ingredient in the oily matrix is to insulate the ingredient from direct contact with moisture due to the hydrophobic characteristics of lipids. That is particularly important for an acid labile pharmaceutical ingredient such as omeprazole, which can be decomposed in moisture, and a conventional gelatin capsule contains an appreciable amount of water (See Pilbrant and Cederberg, *Scand. J. Gastroenterology* (1985) 20:113–120). Therefore, if omeprazole is formulated as a drug mass and being directly in contact with the capsule shell layer, some of the moisture from the gelatin shell layer may leak into the pharmaceutical ingredient mass and cause the ingredient to decompose during storage time.

The oily matrix and pharmaceutical ingredient-filled capsule is finally coated with an enteric coating layer. An enteric coating helps to control the release of the pharmaceutical ingredient in the small intestine, which is at neutral pH.

The enteric coating materials are made of polymers. There are two major kinds of enteric coating polymers: (1) Carbohydrates polymers, which include cellulose acetate phthalate, cellulose acetate succinate, cellulose hydrogen phthalate, cellulose acetate trimellitate, ethyl cellulose, hydroxypropylmethylcellulose phthalate, hydroxypropylmethylcellulose acetate succinate, carboxymethyl ethylcellulose, starch acetate phthalate, and amylose acetate phthalate. (2) Polyvinyl polymers, which include polyvinyl acetate phthalate, polyvinyl butyrate phthalate, styrenemaleic acid copolymer, methylacrylate-methacrylic acid copolymer (MPM-05), methylacrylate-methacrylic acid-methyl-methacrylate copolymer (MPM-06), and methylmethacrylate-methacrylic acid copolymer (Eudragit L & S).

Optionally, the enteric coating can contain a pharmaceutically acceptable plasticizer such as cetanol, triacetin, triethyl citrate, and diethyl phthalate. Occasionally, dispersants such as talc, colorants, and pigments, may also be included in the enteric coating.

The enteric coating is applied onto the capsule by conventional coating techniques such as immersion, pan coating, centrifugation, or fluidized bed coating using solutions of the enteric coating polymers in water and/or suitable organic solvents or by using latex suspensions of the polymers.

There are two methods for making the pharmaceutical preparation. In the first method, the active pharmaceutical ingredient is first mixed with the oily matrix. Then, the mixture is filled into a capsule. Finally, the capsule is coated with an enteric coating.

In the second method, the oily matrix is first filled into a capsule. Then, the active pharmaceutical ingredient is added to the oily matrix-filled capsule. Finally, the capsule is coated with an enteric coating.

The pharmaceutical preparation of the present invention is further specially designed to orally administered omeprazole to patients with gastrointestinal disorders. It can be administered to patients several times a day. The typical daily dose of the active ingredient varies and depends upon various factors of the patients, such as the individual requirements, the kind or severity of the diseases. In the case of adults, the daily dose is in the range of 1–100 mg, preferably at 20 mg.

The pharmaceutical preparation of the present invention is described in detail in the experimental examples set forth below. These examples are for illustration purpose. They should not be construed as defining the scope of the invention.

In each example, two tests were conducted to determine (1) the dissolution rate of the pharmaceutical ingredient; and (2) the integrity of the enteric coated capsule.

Dissolution Test

The dissolution test is conducted according to the USP XXIII Enteric Coated Dissolution Method B. Typically, the enteric coated capsule is placed inside a hollow spiral steel device (so as to prevent the capsule from floating out of the water) which is contained in a water bath. The temperature of the water bath is set at 37±0.5° C. The water bath is set to rotate at 50 rpm. The test contains two stages. At the first stage, the enteric coated capsule is put in the water bath containing 1000 ml of 0.1 N HCl and rotated at 50 rpm for 2 hours. Then, the HCl solution is aspirated out and replaced with 1000 ml of phosphate buffer (pH 6.8) to continue the second stage of the dissolution test. The pharmaceutical ingredient leaking out to the water bath is determined based on UV quantitation method.

Interity Test of the Enteric Coated Capsule: To test whether the enteric coating has damaged the capsule, yellow pigment No. 5 is placed inside the capsule to replace the pharmaceutical ingredient. The capsule is sealed in the same manner as in the actual pharmaceutical preparation. Then, the enteric coating material is coated onto the capsule. This enteric coated capsule is placed in the hollow spiral steel device in the water bath containing 0.1 N of HCl and rotated for 2 hours. An aliquot of sample from the solution is taken out and analyzed by UV quantitation method. This test is designed to determine whether enteric coating can resist acidic condition.

EXPERIMENTAL EXAMPLE 1

Formulation

| Filling Materials: | |
| --- | --- |
| Omeprazole | 20 mg |
| Mineral Oil | 40 mg |
| Enteric Coating Material: | |
| Eudragit L 100 | 20% (w/v) in 1:1 of acetone: isopropanol |

Method

Twenty (20) mg of omeprazole was mixed with 40 mg of mineral oil. The mixture was transferred to a hard capsule and then the capsule was sealed tightly. Alternatively, the mineral oil could be placed inside the capsule, followed by the addition of omeprazole, before the sealing of the capsule.

A 20% (w/v) enteric coating material was prepared by mixing Eudragit L100 in a solvent containing acetone : isopropyl alcohol=1:1 (v/v) solvents. The enteric coating material was coated onto the capsule three times using a fluidized bed apparatus (i.e., a Glatt machine). The enteric coated omeprazole capsule was stored at 40° C. for 2 months. During this period, the exterior appearance of the capsules, the texture of the enteric coated capsule and the wholeness of the capsules (including dissolution and integrity determinations) were monitored. The exterior appearance and the texture of the enteric coated capsule did not show significant change during the course of storage.

Results

The result of the dissolution test is shown in FIG. 1. The result indicates that no significant difference in the dissolution rate during the course of storage. The result of the integrity test shows no leakage of the enteric coated capsule.

EXPERIMENTAL EXAMPLE 2

Formulation

| Filling Materials: | |
| --- | --- |
| Omeprazole | 20 mg |
| Mineral Oil | 40 mg |
| Enteric Coating Material: | |
| Cellulose Acetate Phthalate | 10% (w/v) in 1:1 of acetone: isopropanol |

Method

The preparation was the same as shown in Experimental Example 1 except that a 10% (w/v) of cellulose acetate phthate was used as the enteric coating material.

Results

Figure 2:
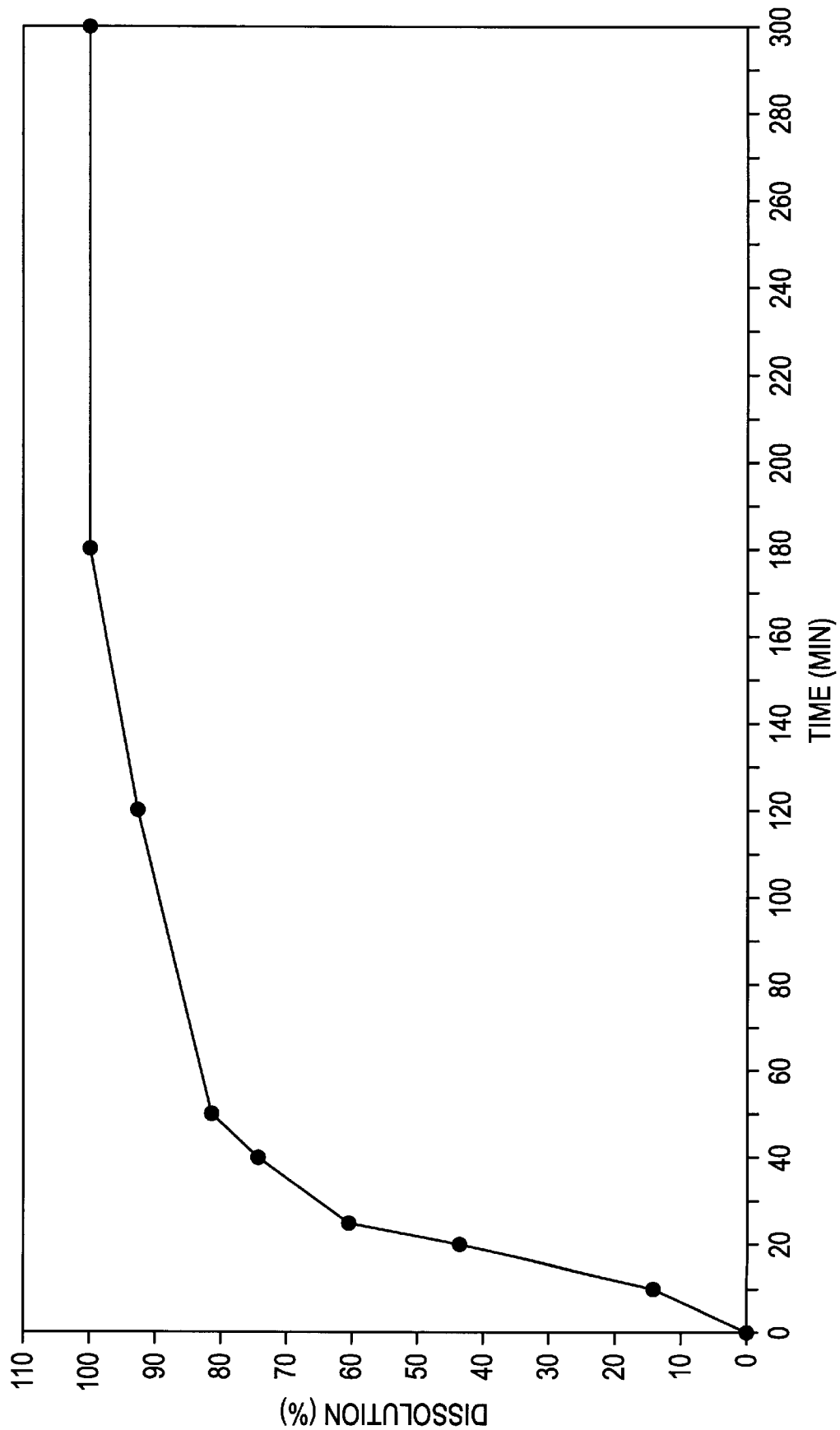
FIG. 2 shows the results of an in vitro dissolution test (% dissolution) for the enteric coated pharmaceutical preparation according to Example 2 (infra). The experimental design was the same as that described in FIG. 1.

The result of the dissolution test of Experimental Example 2 is shown in FIG. 2, which is similar to that shown in Experimental Example 1.

EXPERIMENTAL EXAMPLE 3

Formulation

| Filling Materials: | |
| --- | --- |
| Omeprazole | 20 mg |
| Mineral Oil | 40 mg |
| Enteric Coating Material: | |
| Ethyl Cellulose | 5% (w/v) in 1:1 of acetone: isopropanol |

Method

The preparation was the same as shown in Experimental Example 1 except that a 5% (w/v) of ethyl cellulose was used as the enteric coating material.

Results

Figure 3:
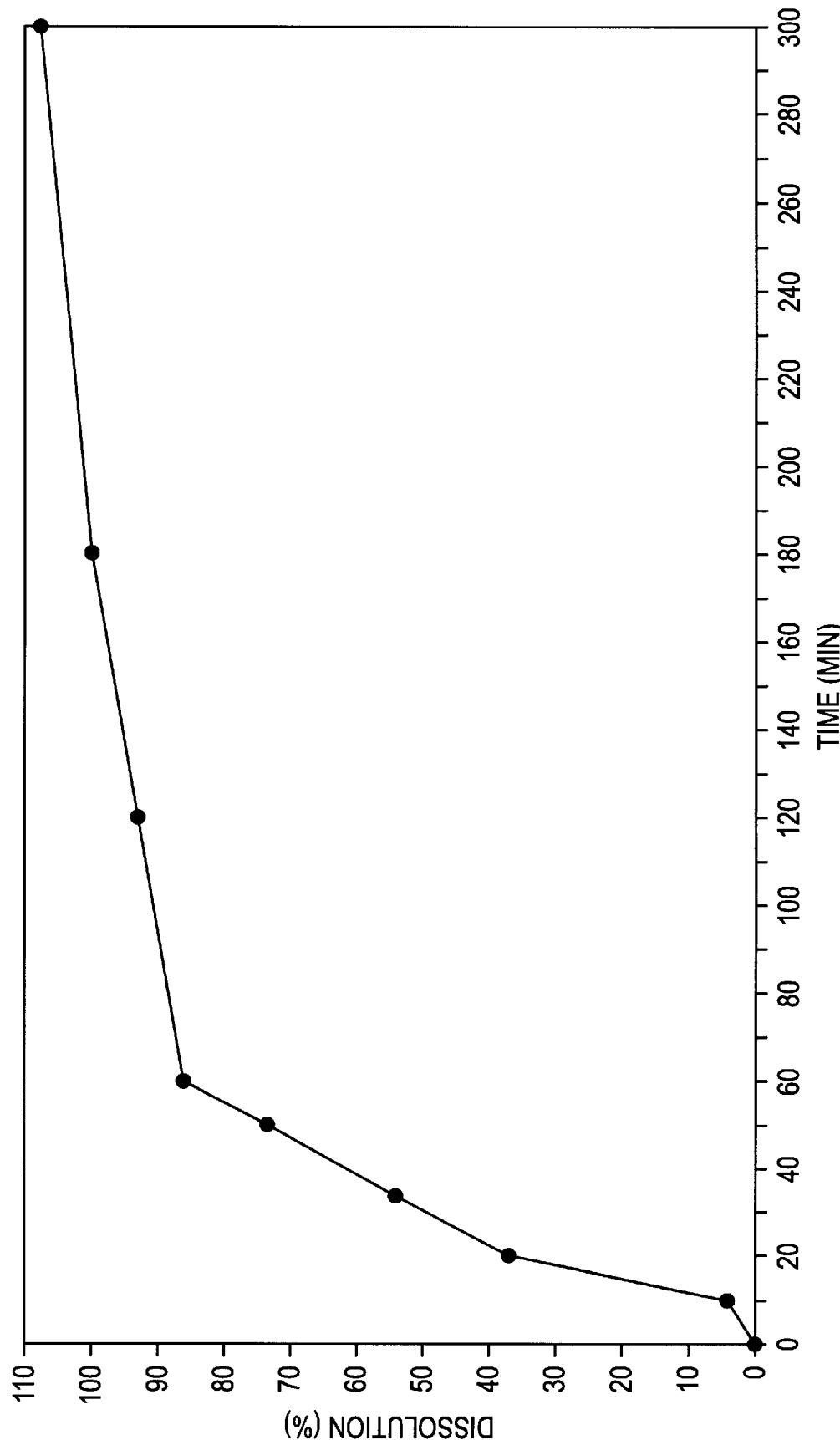
FIG. 3 shows the results of an in vitro dissolution test (% dissolution) for the enteric coated pharmaceutical preparation according to Example 3 (infra). The experimental design was the same as that described in FIG. 1.

The result of the dissolution test of Experimental Example 3 is shown in FIG. 3, which is also similar to that of Experimental Example 1.

EXPERIMENTAL EXAMPLE 4

Formulation

| Filling Materials: | |
| --- | --- |
| Omeprazole | 20 mg |
| Mineral Oil | 40 mg |
| Enteric Coating Material: | |
| Hydroxypropyl methylcellulose phthate | 10% (w/v) in 1:1 of acetone: isopropanol |

Method

The preparation was the same as shown in Experimental Example 1 except that a 10% (w/v) of hydroxypropyl methylcellulose phthate was used as the enteric coating material.

Results

Figure 4:
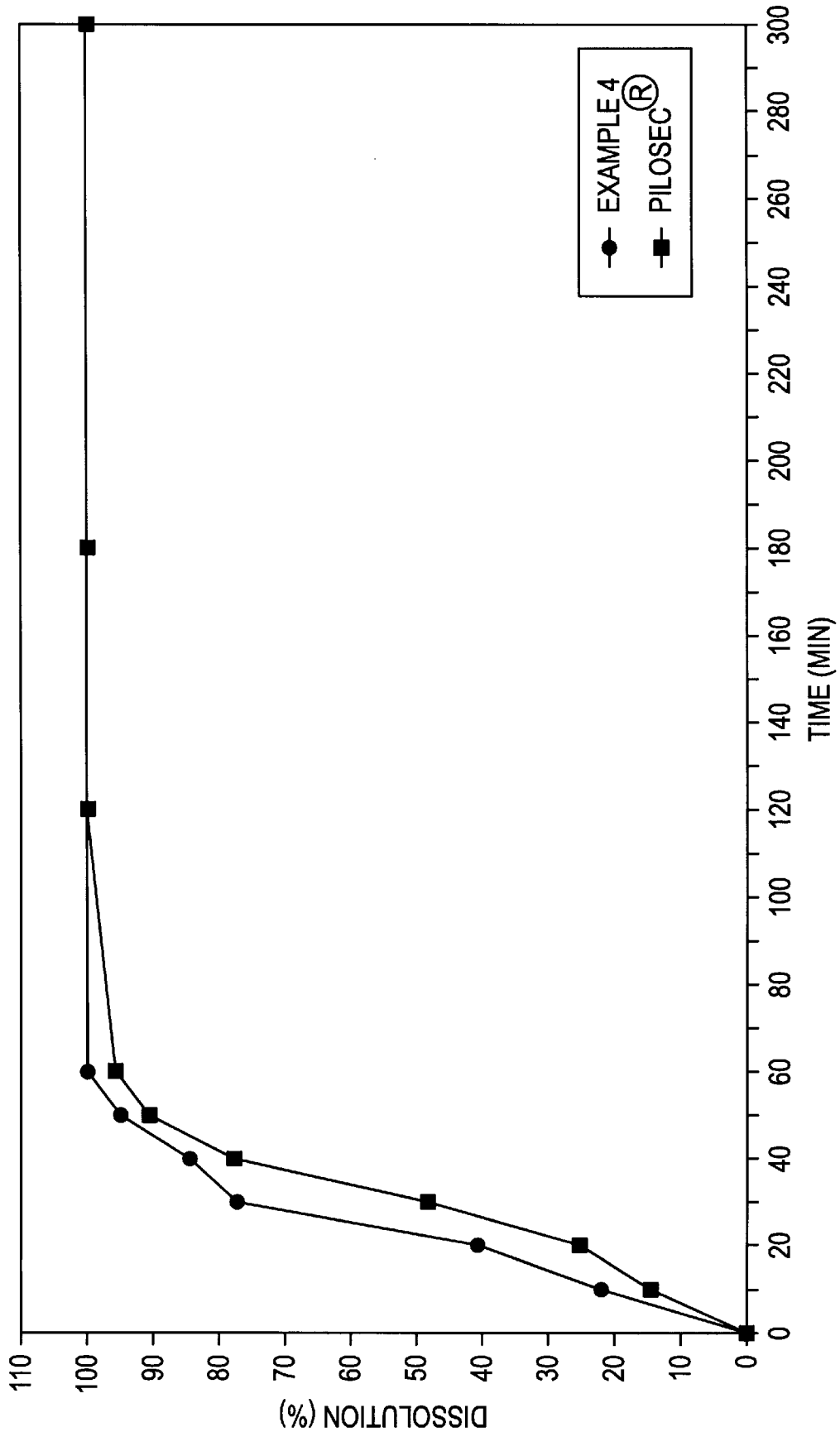
FIG. 4 shows a comparative study on % dissolution between the enteric coated pharmaceutical preparation according to Example 4 (infra) and Pilosec®.

The result of the dissolution test Experimental Example 4 is shown in FIG. 4, which is also similar to that of Experimental Example 1. The dissolution rate (% dissolution) of Experimental Example 4 is further compared with the dissolution rate of Piloseco®, which is the brand name omeprazole sold in the U.S.A. The result (FIG. 4) shows that the dissolution rate of Experimental Example 4 demonstrates much higher dissolution rate than that of Piloseco® during the first 60 minutes of the dissolution.

Other Studies

Studies using other oily matrix, such as paraffin, vaseline, sesame oil, hydrogenated vegetable oil, etc. were undertaken. The enteric coated omeprazole capsules containing various oily matrix were monitored for the changes in the appearance and texture of the capsules after being stored at 40° C. for 2 months. The dissolution rate and integrity of these capsules were also studied. The results show that these omeprazole capsules were not significantly different from those of Experimental Examples 1–4. These results further confirmed that lipids containing low acidic valence or long chain hydrocarbons were most likely to be suitable for the present pharmaceutical preparation.

Pharmacokinetics of the Pharmaceutical Preparation

The pharmaceutical preparation as shown in Experimental Example 4 was further used for studies of pharmacokinetics of omeprazole. Three (3) healthy volunteers, aged between 25 and 30, weight varied within 10%, were given one dose of the omeprazole formulation as shown in Experimental Example 4 in the morning. Before this test, the volunteers have not taken any medicine for 1 week. They also have not taken any stimulating drug for 1 month. On the day of the experiment, the volunteers were fasted overnight. Also, prior to the test, no food was allowed to the volunteers. Before the omeprazole capsule was given, 20 ml of blood were drawn from each volunteer. After the administration of the omeprazole capsule, 10 ml of blood were drawn every half to one hour. The test was completed in 24 hours. The blood collected from the test was centrifuged and the collected serum was stored in the refrigerator. The amount of omeprazole in the serum was determined by HPLC method.

The results of the pharmacokinetic studies of the enteric coated omeprazole capsules as described in Experimental Example 4 are shown in Table 1. These results are further compared to the pharmacokinetic studies of the brand name omeprazole capsule Pilosec®.

TABLE 1

Pharmacokinetics of Omeprazole Capsule in Experimental Example 4 and the Pilosec ® omeprazole capsules

| Kinetic Constant | Example 4 | Pilosec |
| --- | --- | --- |
| Cmax ($\mu$g/mL) | 3.876 | 1.7 |
| AUC ($\mu$g · hr/mL) | 9.15 | 3.1 |
| Ka (hr-1) | 1.596 | 0.36 |
| Kel (hr-1) | 0.5861 | 0.25 |
| t 1/2 (hr) | 0.7669 | 2.77 |

The results of Table 1 show that the maximum omeprazole concentration (Cmax), the bioavailability of omeprazole (as indicated in AUC [i.e., area under curve]), the rate of omeprazole absorption (Ka), the rate of omeprazole elimination (Kel) in sera of volunteers taking the enteric coated omeprazole capsules made by the present preparation were far much greater than those of Pilosec®, suggesting that the omeprazole capsules made by the present preparation have much greater bioavailability and higher absorption rate than Pilosec®. This suggestion was further confirmed by the finding that the half life (t½) of the omeprazole capsules made by the present preparation was much shorter than that of Pilosec® (0.7669 vs. 2.77). It is likely that the lipid used in the preparation contributes to the fast absorption of omeprazole in vivo.

While the invention has been described by way of examples and in terms of the preferred embodiments, it is to be understood that the invention is not limited to the disclosed embodiments. On the contrary, it is intended to cover various modifications as would be apparent to those skilled in the art. Therefore, the scope of the appended claims should be accorded the broadest interpretation so as to encompass all such modification.

What is claimed is:

1. An oral pharmaceutical preparation comprising:
   an active pharmaceutical ingredient embedded in an oily matrix, wherein said active pharmaceutical ingredient is an acid labile or base labile pharmaceutical ingredient which is one selected from the group consisting of a substituted benzimidazole, an ester, a lactone, an amide, a lactam, an oxime, an imide, a malonic urea, a phenol, a catecholamide, an ether, a thiol, a thioether, a carboxylic acid, a nitrite, or an aldehyde;
   wherein said substituted benzimidazole is a free base omeprazole;
   said oily matrix-embedded active pharmaceutical ingredient being enclosed in a capsule; and
   said capsule being coated by an enteric coating.

2. The oral pharmaceutical preparation according to claim 1, wherein the weight ratio of said active pharmaceutical ingredient to said oily matrix ranges from 1:1 to 1:5.

3. The oral pharmaceutical preparation according to claim 1, wherein said oily matrix comprises at least one selected from the group consisting of mineral oil, hydrogenated vegetable oil, paraffin, squalane, vaseline, and lanolin.

4. The oral pharmaceutical preparation according to claim 3, wherein said oily matrix is at about neutral pH.

5. The oral pharmaceutical preparation according to claim 1, said oily matrix-embedded pharmaceutical ingredient further comprising an excipient.

6. The oral pharmaceutical preparation according to claim 2, wherein said excipient comprises at least one selected from the group consisting of lactose, sucrose, sorbital, mannital, starch, amylopectin, cellulose, microcrystalline cellulose, talc, gelatin, and polyvinyl alcohol.

7. The oral pharmaceutical preparation according to claim 1, wherein said capsule is a hard capsule or a soft capsule.

8. The oral pharmaceutical preparation according to claim 7, wherein said capsule is selected from the group consisting of gelatin, pectin, casein, collagen, protein, modified starch, polyvinyl pyrrolidone.

9. The oral pharmaceutical preparation according to claim 1, wherein said enteric coating comprises at least one polymer which is selected from the group consisting of at least a polymer which is selected from the group consisting of cellulose acetate phthalate, cellulose acetate succinate, cellulose hydrogen phthalate, cellulose acetate trimellitate, ethyl cellulose, hydroxypropylmethylcellulose phthalate, hydroxypropyl-methylcellulose acetate succinate, carboxymnethyl ethylcellulose, starch acetate phthalate, amylose acetate phthalate, polyvinyl acetate phthalate, polyvinyl butyrate phthalate, styrene-maleic acid copolymer, methylacrylate-methacrylic acid copolymer, methylacrylate-methacrylic acid-methylmethacrylate copolymer, and methylmethacrylate-methacrylic acid co-polymer.

10. The oral pharmaceutical preparation according to claim 9, wherein said enteric coating further comprises a plasticizer.

11. The oral pharmaceutical preparation according to claim 10, wherein said plasticizer is one selected from the group consisting of triethyl citrate, triacetin, and diethyl phthalate.

12. A method for preparing an oral pharmaceutical preparation according to claim 1, comprising:
    mixing an active pharmaceutical ingredient with an oily matrix to form an oily matrix embedded pharmaceutical complex;
    filling a capsule with the oily matrix embedded-pharmaceutical complex; and
    coating said capsule with an enteric coating.

13. The method for preparing an oral pharmaceutical preparation according to claim 12, wherein the enteric coating is coated onto the capsule by immersion, film-coating, fluidized bed apparatus, or centrifugation method.

14. The method for preparing an oral pharmaceutical preparation according to claim 12, wherein said oily matrix-embedded pharmaceutical complex contains no more than 1.4% by weight of water.

15. A method for preparing an oral pharmaceutical preparation according to claim 1, comprising:
    filling a capsule with an oily matrix;
    adding an acid labile pharmaceutical ingredient to the oily matrix-filled capsule to form an oily matrix-embedded pharmaceutical complex; and
    coating said oily matrix-embedded pharmaceutical complex capsule with an enteric coating.

16. The method for preparing an oral pharmaceutical preparation according to claim 15, wherein the enteric coating is coated onto the capsule by immersion, pan coating, centrifugation, or using fluidized bed apparatus.

17. The method for preparing an oral pharmaceutical preparation according to claim 15, wherein said oily matrix-embedded pharmaceutical complex contains no more than 1.4% by weight of water.

18. A method for the treatment of gastrointestinal diseases comprising administering to a host in need of such treatment a therapeutically effective amount of an oral pharmaceutical preparation according to claim 1.

* * * * *